(12) United States Patent
Dawant et al.

(10) Patent No.: US 7,957,808 B2
(45) Date of Patent: Jun. 7, 2011

(54) SYSTEM AND METHODS OF DEEP BRAIN STIMULATION FOR POST-OPERATION PATIENTS

(75) Inventors: Benoit M. Dawant, Nashville, TN (US); Pierre-Francois Dominique D'Haese, Nashville, TN (US); Peter E. Konrad, Old Hickory, TN (US)

(73) Assignee: Vanderbilt University, Nashville, TN (US)

( * ) Notice: Subject to any disclaimer, the term of this patent is extended or adjusted under 35 U.S.C. 154(b) by 726 days.

(21) Appl. No.: 11/653,599

(22) Filed: Jan. 16, 2007

(65) Prior Publication Data
US 2007/0185544 A1    Aug. 9, 2007

Related U.S. Application Data

(60) Provisional application No. 60/758,882, filed on Jan. 13, 2006.

(51) Int. Cl.
*A61N 1/18*    (2006.01)
(52) U.S. Cl. .......... 607/45; 382/128; 600/378; 600/437; 600/439; 600/544
(58) Field of Classification Search .................. 382/128, 382/131; 600/378, 437, 439, 440, 544; 607/45, 607/116, 139
See application file for complete search history.

(56) References Cited

U.S. PATENT DOCUMENTS

| 2004/0116978 | A1 | 6/2004 | Bradley |
| 2005/0004617 | A1* | 1/2005 | Dawant et al. .................. 607/45 |
| 2005/0043774 | A1 | 2/2005 | Devlin et al. |
| 2005/0070781 | A1 | 3/2005 | Dawant et al. |
| 2006/0004422 | A1 | 1/2006 | De Ridder |

OTHER PUBLICATIONS

Krik Finnis, Yves Starreveld, Andrew Parrent, Abbas Sadikot, and Terry Peters, Three-Dimensional Database of Subcortical Electrophysiological for Image-Guided Stereotactic Funcational Neurosurgery, 2003, IEEE Transactions on Medical Imaging, vol. 22, 93-104.*
P. Pollak, P. Krack, V. Fraix, et al. "*Intraoperative micro- and macrostimulation of the STN in Parkinson's disease*," Mov Disorders, 2002; vol. 17 (Suppl. 3):S155-S161.
J. Volkmann, J. Herzog, F. Kopper, G. Deuschl "*Introduction to the programming of deep brain stimulation*," Mov Disord 2002; vol. 17 (Suppl. 3):S181-S187.
R. G. Deuschl, J. Volkmann, and P. Krack, "*Deep brain stimulation for movement disorders*," Movement Disorders, vol. 17, No. 3, pp. SI, Mar./Apr. 2002.
B. Schrader, W. Hamel, D. Weinert, and H. M. Mehdorn, "*Documentation of electrode localization*," Movement Disorders, vol. 17, No. 3, pp. S167-S174, 2002.

(Continued)

*Primary Examiner* — Carl H Layno
*Assistant Examiner* — Jennifer Stewart
(74) *Attorney, Agent, or Firm* — Tim Tingkang Xia; Morris, Manning & Martin, LLP

(57) ABSTRACT

A method for programming a deep brain stimulator implanted in a target region of a brain of a living subject. In one embodiment, the method comprises the steps of creating an efficacy atlas; acquiring a position of each electrode contact of the at least one electrode; mapping the acquired position of each electrode contact of the at least one electrode onto a corresponding position in the efficacy atlas so as to determine the efficacy of stimulation at the acquired position; and selecting one or more electrode contacts having the highest efficacy for stimulation.

17 Claims, 8 Drawing Sheets
(5 of 8 Drawing Sheet(s) Filed in Color)

OTHER PUBLICATIONS

Rui Lee, "*Automatic placement of regions of interest in medical images using image registration*," Master thesis in Electrical Engineering 2001.

G. K. Rohde, A. Aldroubi, and B. M. Dawant, "*The adaptive bases algorithm for intensity based nonrigid image registration*," IEEE Transactions on Medical Imaging, vol. 22, pp. 1470-1479, 2003.

P.F. D'Haese, E. Cetinkaya, P.E. Konrad, C. Kao, B.M. Dawant, "*Computer-aided placement of deep brain stimulators: from planning to intraoperative guidance*," IEEE Transactions on Medical Imaging, vol. 24 (11), pp. 1469-1478, Nov. 2005.

J. M. Fitzpatrick, P. E. Konrad, C. Nickele, E. Cetinkaya, and C. Kao, "*Accuracy of customized miniature stereotactic platforms*," Sterotact Funct Neurosurg 2005: 83:25-31.

* cited by examiner

SYSTEM AND METHODS OF DEEP BRAIN STIMULATION FOR POST-OPERATION PATIENTS

CROSS-REFERENCE TO RELATED PATENT APPLICATION

This application claims the benefit, pursuant to 35 U.S.C. §19(e), of U.S. provisional patent application Ser. No. 60/758,882, filed Jan. 13, 2006, entitled "SYSTEM AND METHODS OF DEEP BRAIN STIMULATION FOR POST-OPERATION PATIENTS," by Benoit M. Dawant, Pierre-Francois Dominique D'Haese, and Peter E. Konrad, which is incorporated herein by reference in its entirety.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [7] represents the 7th reference cited in the reference list, namely, P. F. D'Haese, E. Cetinkaya, P. E. Konrad, C. Kao, B. M. Dawant, "Computer-aided placement of deep brain stimulators: from planning to intraoperative guidance" IEEE Transactions on Medical Imaging, vol. 24 (11), pp. 1469-78, November 2005.

STATEMENT OF FEDERALLY-SPONSORED RESEARCH

This invention was made with Government support under contract No. IR21 CA89657-01A2 awarded by the National Institute of Health and National Cancer Institute. The Government has certain rights in the invention.

FIELD OF THE INVENTION

The present invention generally relates to deep brain stimulation, and in particular to system and methods of deep brain stimulation for post-operation patients.

BACKGROUND OF THE INVENTION

Since its first Food and Drug Administration (FDA) approval in 1998, deep brain stimulation (DBS) has gained significant popularity in the treatment of a variety of brain-controlled disorders, including movement disorders [3, 4]. The therapy of the DBS has significant applications in the treatment of tremor, rigidity, and drug induced side effects in patients with Parkinson's disease and essential tremor. Such treatment involves placement of a DBS electrode lead through a burr hole drilled in the patient's skull, and then applying appropriate stimulation signals through the electrode lead to the physiological target.

Usually, after the surgery of DBS implantation, the patient leaves the hospital with the stimulation system such as an internal pulse generator turned off, since transient lesional effects associated with microscopic brain edema caused by the surgery may interfere with DBS programming and lead to multiple adjustments in the parameter settings. The stimulation system is turned on typically about 1-5 weeks after the surgery is performed, for stimulation. This allows the patient to recover from the surgery and provides enough time for the transient lesional effects to resolve. The stimulation is accomplished by programmably applying appropriate stimulation signals to one or more electrode contacts of each implanted electrode. Thus, finding the optimal programming parameters so that it efficiently stimulates the target of interest is crucial to the DBS. Detailed principles and methods used to select the optimal programming parameters have been presented by different authors [1, 2].

Briefly, the first step in postoperative programming is the examination of the effectiveness and side effects induced by each individual contact. The electrode contacts are sequentially evaluated in a monopolar configuration in an effort to determine the contact that produces best compromise. Frequency and pulse width of the stimulation signals are typically kept at constant settings of about 130-180 Hz and about 60-120 µs, respectively. Amplitude is steadily increased to the tolerance level of the patient or until side effects occur. Repeating motor evaluation is then performed to assess the efficacy of stimulation. About ten to 15 minutes are allowed to pass between trials of separate contacts to allow the effects from previous stimulations to disappear. If a satisfactory result cannot be achieved with monopolar stimulation, more complex arrays including bipolar, tri-polar, quadric-polar, or multiple cathodes are tried. The initial programming session, as described above, can take several hours and requires continuous feedback from the patient to ascertain the degree benefits and to identify any side effects. This can be very taxing, especially when patients are kept off of medication for long periods of time. Furthermore, optimal programming may take several trials over many months to achieve, which can be frustrating to both patients and their attending health care professionals.

Automated selection of the optimal contact would facilitate the programming process and reduce the length of time required to determine optimum programming and thus be beneficial to the patients.

Therefore, a heretofore unaddressed need exists in the art to address the aforementioned deficiencies and inadequacies.

SUMMARY OF THE INVENTION

In one aspect, the present invention relates to a method for programming a deep brain stimulator implanted in a target region of a brain of a living subject for optimal stimulation, where the deep brain stimulator comprises at least one electrode having a plurality of electrode contacts spaced apart from each other, and any portion of the brain of the living subject is identifiable by a set of corresponding spatial coordinates.

In one embodiment, the method includes the steps of (i) creating an efficacy atlas in which any spatial coordinates for a position in a target region of the brain of the living subject are related to a position with corresponding atlas coordinates in the efficacy atlas, and each position in the atlas coordinates of the efficacy atlas is associated with an efficacy of stimulation at a corresponding position in the spatial coordinates of the brain of the living subject; (ii) acquiring a position of each electrode contact of the at least one electrode in the spatial coordinates of the brain of the living subject; (iii) mapping the acquired position of each electrode contact of the at least one electrode in the spatial coordinates of the brain of the living subject onto a corresponding position in the efficacy atlas so as to determine the efficacy of stimulation at the acquired position in the spatial coordinates of the brain of the living subject; and (iv) selecting one or more electrode contacts having the highest efficacy for stimulation.

In one embodiment, the mapping step is performed with a non-rigid registration algorithm.

In one embodiment, the efficacy atlas comprises at least one stimulation map having at least one stimulation region corresponding to the target region of the brain of the living subject for optimal stimulation.

The efficacy of stimulation at a position is corresponding to the probability of the stimulation to be clinically effective at the position. In one embodiment, the efficacy of stimulation at a position in the spatial coordinates of the brain of the living subject is (1) proportional to a percent of loss of rigidity, $L^R$; (2) proportional to a therapeutic window that equals to the difference between a voltage, V, applied to the position for achieving the loss of rigidity and a voltage, $V^{SE}$, applied to the position for which side effects occur; and (3) inversely proportional to the voltage V.

In one embodiment, the creating step comprises the steps of:

(a). obtaining stimulation data corresponding to a target region in which a deep brain stimulator is implanted from a database, where the stimulation data comprise M×N sets of intra-operatively acquired stimulation signals, $\{V_{ij}, L_{ij}^R, V_{ij}^{SE}\}$, and their corresponding stimulation positions, $\{x_j, y_j, z_j\}$, where i=1, 2, . . . , M, M being a positive integer and the number of a population of living subjects from which the stimulation signals are acquired and stored in the database, and j=1, 2, . . . , N, N being a positive integer and the number of positions at which the stimulation takes place for each of the population of living subjects, and where $V_{ij}$, $L_{ij}^R$, $V_{ij}^{SE}$ are a stimulation voltage, a percent of loss of rigidity caused by the stimulation voltage, and a voltage for which side effects occur, respectively, at the j-th stimulation position of the i-th living subject;

(b). choosing a local efficacy of stimulation, $E_{ij}$, at the j-th stimulation position $(x_j, y_j, z_j)$ for the i-th living subject with a Gaussian curve, $F_{ij}$, in the form of:

$$F_{ij} = E_{ij} * \exp\left[-\left(\frac{x_j^2 + y_j^2 + z_j^2}{2V_{ij}^2}\right)\right],$$

where the local efficacy of stimulation $$E_{ij} = L_{ij}^R * (V_{ij}^{SE} - V_{ij}) * \frac{1}{V_{ij}},$$

and the height of the Gaussian curve $F_{ij}$ is a function of the local efficacy of stimulation $E_{ij}$, and the radius of the Gaussian curve $F_{ij}$ is a function of the stimulation voltage $V_{ij}$;

(c). repeating step (b) for each of the population of living subjects, i=1, 2, . . . , M, so as to obtain M sets of Gaussian curves $\{F_{ij}\}$ for the j-th stimulation position $(x_j, y_j, z_j)$;

(d). averaging the M sets of Gaussian curves $\{F_{ij}\}$ to obtain an efficacy of stimulation at the j-th stimulation position $(x_j, y_j, z_j)$, which is equal to the mean value of the M sets of Gaussian curves $\{F_{ij}\}$; and (e). repeating steps (b)-(d) for each of the stimulation positions, j=1, 2, . . . , N, to obtain N efficacies of stimulation respectively for the N stimulation positions, thereby creating the efficacy atlas.

The database includes an electrophysiological atlas containing electrophysiological information acquired from each of the population of living subjects and related to atlas coordinates of the electrophysiological atlas. The atlas coordinates of the efficacy atlas is substantially coincident with the atlas coordinates of the electrophysiological atlas.

The electrophysiological information comprises at least intra-operative information for each of the population of living subjects. In one embodiment, the intra-operative information comprises at least specific information associated with at least one stimulation electrode, where the specific information includes voltages applied to the at least one stimulation electrode, a response of a living subject undergoing treatment to the stimulation, differences in voltage between disappearance of symptoms and appearance of side effects, and a position of the at least one stimulation electrode, where the response of the living subject undergoing treatment to the stimulation includes loss of rigidity, location where the loss of rigidity is observed, appearance of side effects, and/or location affected by these side effects. In another embodiment, the intra-operative information comprises at least specific information associated with a deep brain stimulator having at least one electrode, where the specific information includes a position of each electrode contact of the at least one electrode, and a voltage, frequency and pulse width of stimulation at the position.

In one embodiment, the acquiring step has the step of obtaining the position of each electrode contact of the at least one electrode from the database. In another embodiment, the acquiring step has the step of acquiring the position of each electrode contact of the at least one electrode post-operatively from the target region of the brain of the living subject in which the deep brain stimulator is implanted.

In another aspect, the present invention relates to a system for programming a deep brain stimulator implanted in a target region of a brain of a living subject for optimal stimulation, where the deep brain stimulator comprises at least one electrode having a plurality of electrode contacts spaced apart from each other, and any portion of the brain of the living subject is identifiable by a set of corresponding spatial coordinates.

In one embodiment, the system has an efficacy atlas in which each position in the atlas coordinates of the efficacy atlas is associated with an efficacy of stimulation at a corresponding position in the spatial coordinates of the brain of the living subject; means for acquiring a position of each electrode contact of the at least one electrode in the spatial coordinates of the brain of the living subject; and a controller at least communicable with the efficacy atlas and adapted for mapping the acquired position of each electrode contact of the at least one electrode in the spatial coordinates of the brain of the living subject onto a corresponding position in the atlas coordinates of the efficacy atlas so as to determine the efficacy of stimulation at the acquired position in the spatial coordinates of the brain of the living subject, and selecting one or more electrode contacts having the highest efficacy for stimulation. In one embodiment, the efficacy atlas is created by steps (a)-(e) as disclosed above.

In one embodiment, the efficacy atlas comprises at least one stimulation map having at least one stimulation region related to the target region of the brain of the living subject for optimal stimulation.

The efficacy of stimulation at a position is corresponding to the probability of the stimulation to be clinically effective at the position. In one embodiment, the efficacy of stimulation at a position in the spatial coordinates of the brain of the living subject is (1) proportional to a percent of loss of rigidity, $L^R$; (2) proportional to a therapeutic window that equals to the difference between a voltage, V, applied to the position for achieving the loss of rigidity and a voltage, $V^{SE}$, applied to the position for which side effects occur; and (3) inversely proportional to the voltage V.

Furthermore, the system has a non-rigid registration algorithm stored in a memory that is in communication with the controller.

Moreover, the system has a data storage device for storing the efficacy atlas, the data storage device configured to be in communication with the controller.

Additionally, the system has a database stored in the data storage device, where the database comprises an electrophysiological atlas containing electrophysiological information acquired from a brain of each of a population of living subjects and related to atlas coordinates of the electrophysiological atlas. In one embodiment, the atlas coordinates of the efficacy atlas is substantially coincident with the atlas coordinates of the electrophysiological atlas.

In one embodiment, the electrophysiological information comprises at least intra-operative information for each of the population of living subjects. In one embodiment, the intra-operative information comprises at least specific information associated with at least one stimulation electrode, where the specific information includes voltages applied to the at least one stimulation electrode, a response of a living subject undergoing treatment to the stimulation, differences in voltage between disappearance of symptoms and appearance of side effects, and a position of the at least one stimulation electrode, where the response of the living subject undergoing treatment to the stimulation includes loss of rigidity, location where the loss of rigidity is observed, appearance of side effects, and/or location affected by these side effects. In another embodiment, the intra-operative information comprises at least specific information associated with a deep brain stimulator implanted in a target region of a brain of a living subject, where the specific information includes a position of each electrode contact of the deep brain stimulator, and a voltage, frequency and pulse width of stimulation at the position.

In one embodiment, the acquiring means comprises a device for obtaining the position of each electrode contact of the at least one electrode from the database. In another embodiment, the acquiring means comprises a device for acquiring the position of each electrode contact of the at least one electrode post-operatively from the target region of the brain of the living subject in which the deep brain stimulator is implanted.

In yet another aspect, the present invention relates to a method for programming a deep brain stimulator implanted in a target region of a brain of a living subject for optimal stimulation, where the deep brain stimulator comprises at least one electrode having a plurality of electrode contacts.

In one embodiment, the method includes the step of creating an efficacy atlas in which a position in atlas coordinates of the efficacy atlas is related to a corresponding position in spatial coordinates of the brain of the living subject, and each position in atlas coordinates of the efficacy atlas is associated with an efficacy of stimulation at a corresponding position in spatial coordinates of the brain of the living subject. In one embodiment, the efficacy atlas is created according to steps (a)-(e) disclosed above.

In one embodiment, the efficacy atlas comprises at least one stimulation map having at least one stimulation region related to the target region of the brain of the living subject for optimal stimulation.

The method further includes the steps of mapping a position of each electrode contact of the at least one electrode in the spatial coordinates of the brain of the living subject onto a corresponding position in the atlas coordinates of the efficacy atlas so as to determine the efficacy of stimulation at the acquired position in the spatial coordinates of the brain of the living subject; and selecting one or more electrode contacts having the highest efficacy for stimulation, where the mapping step is performed with a non-rigid registration algorithm.

In a further aspect, the present invention relates to a system for programming a deep brain stimulator implanted in a target region of a brain of a living subject for optimal stimulation, where the deep brain stimulator comprises at least one electrode having a plurality of electrode contacts spaced apart from each other, and where any portion of the brain of the living subject is identifiable by a set of corresponding spatial coordinates.

In one embodiment, the system has a data storage device; a database stored in the data storage device, comprising an electrophysiological atlas containing electrophysiological information acquired from each of the population of living subjects and related to atlas coordinates of the electrophysiological atlas; and a controller in communication with the data storage device and adapted for programmably interfacing with the database for creating an efficacy atlas in which a position in atlas coordinates of the efficacy atlas is related to a corresponding position in spatial coordinates of the brain of the living subject, and vice versa, and each position in atlas coordinates of the efficacy atlas is associated with an efficacy of stimulation at a corresponding position in spatial coordinates of the brain of the living subject.

The controller is also adapted for programmably mapping a position of each electrode contact of the at least one electrode in the spatial coordinates of the brain of the living subject onto a corresponding position in the atlas coordinates of the efficacy atlas so as to determine the efficacy of stimulation at the acquired position in the spatial coordinates of the brain of the living subject, and selecting one or more electrode contacts having the highest efficacy for stimulation.

The efficacy atlas comprises at least one stimulation map having at least one stimulation region related to the target region of the brain of the living subject for optimal stimulation. The atlas coordinates of the efficacy atlas is substantially coincident with the atlas coordinates of the electrophysiological atlas.

In yet a further aspect, the present invention relates to a system for programming a deep brain stimulator implanted in a target region of a brain of a living subject for optimal stimulation, where the deep brain stimulator comprises at least one electrode having a plurality of electrode contacts, and where any portion of the brain of the living subject is identifiable by a set of corresponding spatial coordinates. In one embodiment, the system includes a data storage device; and an efficacy atlas stored in the data storage device, where each position in atlas coordinates of the efficacy atlas is associated with an efficacy of stimulation at a corresponding position in spatial coordinates of the brain of the living subject.

The system further includes a controller in communication with the data storage device and adapted for programmably mapping a position of each electrode contact of the at least one electrode in the spatial coordinates of the brain of the living subject onto a corresponding position in the atlas coordinates of the efficacy atlas so as to determine the efficacy of stimulation at the acquired position in the spatial coordinates of the brain of the living subject, and selecting one or more electrode contacts having the highest efficacy for stimulation.

In one aspect, the present invention relates to software stored on a computer readable medium for causing a computing system to perform functions comprising: (i) creating an efficacy atlas in which a position in atlas coordinates of the efficacy atlas is related to a corresponding position in spatial coordinates of the brain of the living subject, and each position in the atlas coordinates of the efficacy atlas is associated with an efficacy of stimulation at a corresponding position in the spatial coordinates of the brain of the living subject; (ii) acquiring a position of each electrode contact of the at least one electrode in the spatial coordinates of the brain of the living subject; (iii) mapping the acquired position of each electrode contact of the at least one electrode in the spatial coordinates of the brain of the living subject onto a corresponding position in the atlas coordinates of the efficacy atlas so as to determine the efficacy of stimulation at the acquired position in the spatial coordinates of the brain of the living subject; and (iv) selecting one or more electrode contacts having the highest efficacy for stimulation.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DETAILED DESCRIPTION OF THE INVENTION

Figure 1:
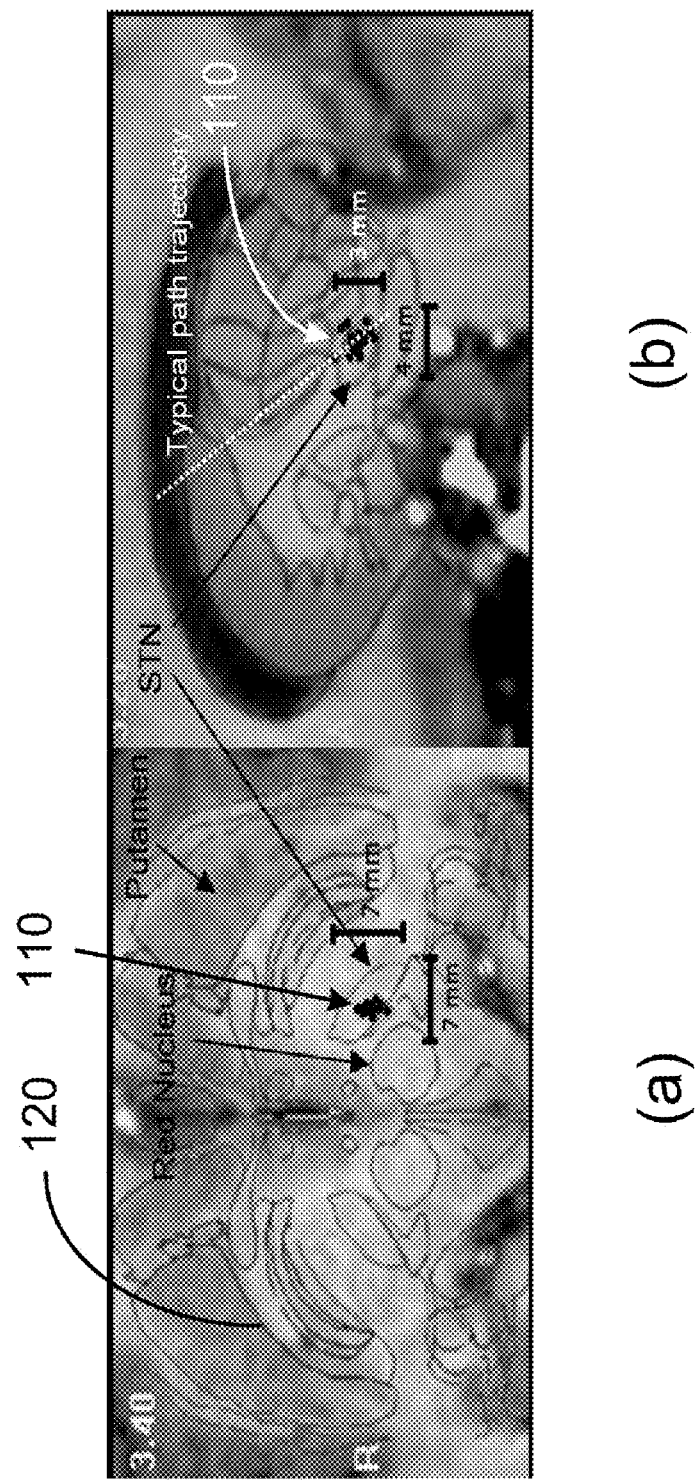
FIG. 1 shows intra-operatively selected DBS target positions (for the right STN) mapped onto an atlas according to one embodiment of the present invention, where the target positions are projected onto the axial (a) and sagittal (b) slices passing through the centroid of the clusters, and contours showing the anatomic structures are obtained from the Shaltenbrand-Wahren atlas.

The present invention is more particularly described in the following examples that are intended as illustrative only since numerous modifications and variations therein will be apparent to those skilled in the art. Various embodiments of the invention are now described in detail. Referring to the drawings of FIGS. 1-8, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

Definitions

The terms used in this specification generally have their ordinary meanings in the art, within the context of the invention, and in the specific context where each term is used.

Certain terms that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

As used herein, "about" or "approximately" shall generally mean within 20 percent, preferably within 10 percent, and more preferably within 5 percent of a given value or range. Numerical quantities given herein are approximate, meaning that the term "about" or "approximately" can be inferred if not expressly stated.

As used herein, the term "living subject" refers to a human being such as a patient, or an animal such as a lab testing monkey.

As used herein, "target," "target of interest," and "target region" are synonyms in the specification and refer to an object of stimulation in a deep brain of a living subject for treatment of a brain-controlled disorder.

As used herein, "stimulation" refers to increase temporarily the activity of a body organ or part thereof responsive to an input signal to the body organ or part.

The terms "project," "map," "register," and "transform," as used herein, are synonyms in the specification and refer to a transformation of a point of interest from a source image volume to a target image volume, and vice versa.

The terms "place," "implant," and "insert," as used herein, are synonyms in the specification and refer to put or embed a device, such as a microelectrode recording lead, macrostimulation lead, and/or a deep brain stimulator, into a target region of a brain of a living subject.

Overview of the Invention

The description will be made as to the embodiments of the present invention in conjunction with the accompanying drawings of FIGS. 1-8. In accordance with the purposes of this invention, as embodied and broadly described herein, this invention, in one aspect, relates to a system for programming a deep brain stimulator implanted in a target region of a brain of a living subject for optimal stimulation. The deep brain stimulator includes at least one electrode having a plurality of electrode contacts spaced apart from each other.

The post-operative neurological management of patients with the STN-DBS for Parkinson's disease is a complex and dynamic process that involves optimizing the stimulation parameters and decreasing the anti-parkinsonian medication while assessing the interactions of both treatment modalities. Neurologists who treat patients undergoing DBS therapy must have expert knowledge of the electroanatomy of the subthalamic area and be familiar with the medical treatment of motor and non-motor symptoms. In clinical practice, finding the optimal programming parameters can be a challenging and time-consuming process. The present invention, among other things, discloses a computerized system to facilitate one of the bottlenecks of DBS therapy: the IPG (Internal Pulse Generator) programming. This system includes an efficacy atlas that is created from a database. The database includes an electrophysiological atlas (deformable physiological atlas) built on more than 300 pieces of intra-operative information acquired from 30 Parkinson's patients and of a non-rigid registration algorithm used to map these data into the atlas. By correlating the position of each electrode contact of a stimulation electrode implanted in a target region of a brain of a patient with the information contained in the atlas, one can determine which of the contacts has the highest probability (efficacy) to be the most clinically effective.

In the electrophysiological atlas, any spatial coordinates of the brain of a patient are related to atlas coordinates in the atlas in a way such that the electrophysiological information associated with spatial coordinates from which it is acquired in the brain of the patient can be related to atlas coordinates in the atlas, and vice versa. The intra-operative information for each patient comprises at least specific information associated with at least one stimulation electrode. The specific information includes, but is not limited to, voltages applied to the at least one stimulation electrode, a response of the patient undergoing treatment to the stimulation, differences in voltage between disappearance of symptoms and appearance of side effects, and a position of the at least one stimulation electrode. The response of the patient undergoing treatment to the stimulation includes loss of rigidity, location where the loss of rigidity is observed, appearance of side effects, and/or location affected by these side effects. Additionally, the intra-operative information for each patient also includes at least specific information associated with a deep brain stimulator implanted in a target region of the brain of the patient, where the specific information includes information about a position of each electrode contact of the deep brain stimulator, and a voltage, frequency and pulse width of stimulation at the position.

The efficacy of stimulation at a position in the spatial coordinates of a brain of a patient is corresponding to the probability of the stimulation to be clinically effective at the position. In general, the efficacy of stimulation at a position is (1) proportional to a percent of loss of rigidity, $L^R$; (2) proportional to a therapeutic window that equals to the difference between a voltage, $V$, applied to the position for achieving the loss of rigidity and a voltage, $V^{SE}$, applied to the position for which side effects occur; and (3) inversely proportional to the voltage V. A position is regarded as an optimal stimulation position if the percentage of the loss of rigidity $L^R$ is high, the applied voltage V is low, and the difference between $V^{SE}$ and V is large. In other words, the stimulation of an electrode contact at such a position has the highest probability to be the most clinically effective.

According to the present invention, an efficacy atlas is created from the electrophysiological atlas. In the efficacy atlas, a position in atlas coordinates in the efficacy atlas is related to a corresponding position in spatial coordinates in a target region of a brain of a patient, and each position in the atlas coordinates of the efficacy atlas is associated with an efficacy of stimulation at a corresponding position in the spatial coordinates of the brain of the patient. The atlas coordinates of the efficacy atlas is substantially coincident with the atlas coordinates of the electrophysiological atlas. The efficacy atlas has at least one stimulation map having at least one stimulation region related to the target region of the brain of the patient for optimal stimulation.

Specifically, the creation of the efficacy map is as follows: at first, stimulation data corresponding to a target region in which a deep brain stimulator is implanted are obtained from the database (electrophysiological atlas). The stimulation data include M×N sets of intra-operatively acquired stimulation signals, $\{V_{ij}, L_{ij}^R, V_{ij}^{SE}\}$, and their corresponding stimulation positions, $\{x_j, y_j, z_j\}$, mapped onto the electrophysiological atlas, where i=1, 2, ..., M, M being a positive integer and the number of a population of patients from which the stimulation signals are acquired and stored in the database, In this example, M=30. j=1, 2, ..., N, N being a positive integer and the number of positions at which the stimulation takes place for each of the population of patients. $V_{ij}, L_{ij}^R, V_{ij}^{SE}$ are a stimulation voltage, a percent of loss of rigidity caused by the stimulation voltage, and a voltage for which side effects occur, respectively, at the j-th stimulation position of the i-th patient.

Secondly, a local efficacy of stimulation, $E_{ij}$, at the j-th stimulation position $(x_j, y_j, z_j)$ for the i-th patient is modeled with a Gaussian curve, $F_{ij}$. The Gaussian curve $F_{ij}$ is defined to be the form of:

$$F_{ij} = E_{ij} * \exp\left[-\left(\frac{x_j^2 + y_j^2 + z_j^2}{2V_{ij}^2}\right)\right],$$

where the local efficacy of stimulation $$E_{ij} = L_{ij}^R * (V_{ij}^{SE} - V_{ij}) * \frac{1}{V_{ij}},$$

and the height of the Gaussian curve $F_{ij}$ is a function of the local efficacy of stimulation $E_{ij}$, and the radius of the Gaussian curve $F_{ij}$ is a function of the stimulation voltage $V_{ij}$.

Then, repeatedly modeling the efficacy of stimulation at the j-th stimulation position $(x_j, y_j, z_j)$ for each of the population of patients, i=1, 2, ..., M, results in M sets of Gaussian curves $\{F_{ij}\}$ for the j-th stimulation position $(x_j, y_j, z_j)$. The M sets of Gaussian curves $\{F_{ij}\}$ are averaged to obtain an efficacy of stimulation at the j-th stimulation position $(x_j, y_j, z_j)$, which is equal to the mean value of the M sets of Gaussian curves $\{F_{ij}\}$.

Repeating the above processes for each of the stimulation positions, j=1, 2, ..., N, to obtain N efficacies of stimulation respectively at the N stimulation positions, thereby creating an efficacy atlas in which any spatial coordinates of the brain of the patient are related to atlas coordinates of the efficacy atlas, and each position in the atlas coordinates of the efficacy atlas is associated with an efficacy of stimulation at a corresponding position in the spatial coordinates of the brain of the patient.

Accordingly, a point (position) with a small stimulation voltage and a high percentage of the loss of rigidity is thus associated with a curve with a small standard deviation and large amplitude. In other words, a point (position) associated with a curve that has a small standard deviation and large amplitude has a large but localized effect on the atlas, while a point (position) with a large standard deviation has a smaller impact that extends over a larger region.

Furthermore, the system includes a controller at least communicable with the efficacy atlas and adapted for mapping the position of each electrode contact of the at least one electrode in the spatial coordinates of the brain of the patient onto a corresponding position in the atlas coordinates of the efficacy atlas so as to determine the efficacy of stimulation at the acquired position in the spatial coordinates of the brain of the patient, and selecting one or more electrode contacts having the highest efficacy for stimulation.

The position of each electrode contact of the at least one electrode in the spatial coordinates of a brain of a patient can be obtained directly from the database or acquired post-operatively from the target region of the brain of the patient in which the deep brain stimulator is implanted.

The mapping process is performed with a non-rigid registration algorithm.

Additionally, the system has a data storage device for storing the efficacy atlas, the data storage device configured to be in communication with the controller.

Another aspect of the present invention relates to a method for programming a deep brain stimulator implanted in a target region of a brain of a patient for optimal stimulation, where the deep brain stimulator comprises at least one electrode having a plurality of electrode contacts, and any portion of the brain of the patient is identifiable by a set of corresponding spatial coordinates.

The method, in one embodiment, includes the following steps: at first, an efficacy atlas is created form the database, such that any spatial coordinates for a position in a target region of the brain of the patient are related to a position with corresponding atlas coordinates in the efficacy atlas, and each position in the atlas coordinates of the efficacy atlas is associated with an efficacy of stimulation at a corresponding position in the spatial coordinates of the brain of the patient. Secondly, a position of each electrode contact of the at least one electrode in the spatial coordinates of the brain of the patient is acquired. Next, the acquired position of each electrode contact of the at least one electrode in the spatial coordinates of the brain of the patient is mapped onto a corresponding position in the efficacy atlas so as to determine the efficacy of stimulation at the acquired position in the spatial coordinates of the brain of the patient. Then, one or more electrode contacts having the highest efficacy are selected for stimulation.

An alternative aspect of the present invention relates to software stored on a computer readable medium for causing a computing system to perform functions comprising: (i) creating an efficacy atlas in which a position in atlas coordinates of the efficacy atlas is related to a corresponding position in spatial coordinates of the brain of the patient, and each position in the atlas coordinates of the efficacy atlas is associated with an efficacy of stimulation at a corresponding position in the spatial coordinates of the brain of the patient; (ii) acquiring a position of each electrode contact of the at least one electrode in the spatial coordinates of the brain of the patient; (iii) mapping the acquired position of each electrode contact of the at least one electrode in the spatial coordinates of the brain of the patient onto a corresponding position in the atlas coordinates of the efficacy atlas so as to determine the efficacy of stimulation at the acquired position in the spatial coordinates of the brain of the patient; and (iv) selecting one or more electrode contacts having the highest efficacy for stimulation.

These and other aspects of the present invention are more specifically described below.

IMPLEMENTATIONS AND EXAMPLES OF THE INVENTION

Without intent to limit the scope of the invention, exemplary methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Patients and Data Collection

In one embodiment of the present invention, a population of thirty (30) PD patients undergoing DBS therapy was chosen to gather data for evaluating the invented method. Each patient, or a living subject of study, was assigned a number from P1 to P30 as his or her identification. The data was collected with Vanderbilt University Institutional Review Board (RB) approval (Vanderbilt University IRB No. 010809). Specifically, a set of X-ray computed tomography (CT) and magnetic resonance (MR) image volumes were acquired pre-operatively for each patient with the patient anesthetized and head secured to the table to minimize motion. Typically, the CT images were acquired at kvp=120 V, exposure=350 mas, 512×512 voxels ranging in size from 0.49 to 0.62 mm, and slice thickness from 1 mm to 2 mm; and the MR images were acquired with a 1.5 T GE Signa scanner at 3D SPGR volumes, TR: 12.2, TR: 2.4, dimension 256× 256×124 voxels, typical voxels dimensions 0.85×0.85×1.3 $mm^3$.

The surgical procedures as well as pre- and post-operative evaluations were identical for all the thirty patients. Among them, seventeen of these were followed for a period of at least six (6) months after their DBS implantation and had optimal programming parameters determined by their neurologist or neurosurgeon. The remaining thirteen (13) patients had not gotten long enough follow-ups to achieve stable programming.

Surgical planning and operative procedures performed at Vanderbilt University were described in detail in [7]. Briefly, pre-operative target identification was performed automatically using an atlas-based method. The automatically predicted targets were then checked by the functional neurosurgeon. Each location of the automatically predicted targets was then refined intra-operatively based on the surgical team's interpretation of electrophysiological recordings and responses to stimulations. The surgical team usually included a neurosurgeon, a neurophysiologist, and a neurologist.

The operative procedures in one embodiment, were performed with a miniature stereotactic frame, for example, StarFix microTargeting® Platform® (FHC, Inc., Bowdoinham, Me.), instead of a standard stereotactic frame. The StarFix microTargeting Platform® is also referred as a platform hereinafter. During the surgery, a micro-positioning drive, such as microTargeting® drive, from FHC, Inc., was mounted on the StarFix platform. Recording and stimulating (electrode) leads were then inserted into the target of interest through guiding tubes of the microTargeting® drive. The StarFix platform was uniquely designed, based on pre-operatively acquired CT images from the patient such that the pre-operative predicted target was located on the central track. Details on the platform, including a study of its accuracy that shows it to be at least as accurate as standard frames were described in [8]. The position of the electrode lead was read from the micro-positioning device and converted into a (x, y, z) position in CT coordinates. The position of each contact of the electrode lead was then computed using the geometry of the electrode lead and the final intra-operative position of the center of the DBS implant in CT coordinates. In one embodiment, the DBS implants used for these patients were the Medtronic 3389 quadripolar Lead® (Medtronic, Inc., Minneapolis, Minn.), where the size of each contact is 0.5 mm and the gaps between two adjacent contacts are 0.5 mm. Other DBS implants can also be utilized to practice the present invention.

It should be noted that according to the present invention, the data collection, atlas and DBS programming are independent of what frame (platform) or frame-less based system one uses to implant the DBS leads.

Rigid and Non-Rigid Registration Algorithms

According to the present invention, all information acquired from a population of patients needs to be mapped an atlas. The atlas is a common frame of reference in which the position of each individual DBS can be recorded. Creation of the atlas requires registering individual image volumes to a common reference volume, which corresponds to the spatial normalization of each individual brain image. Two types of registrations algorithms, rigid and non-rigid, are utilized to achieve this goal. The rigid registration algorithm is required to register MR and CT image volumes of the same patient. It is necessary because, as described above, the intra-operative positions of the electrode contacts provided by the micro-positioning drive are in CT coordinates. The algorithm used to register MR and CT images of the same patient is an independent implementation of a standard Mutual Information-based algorithm [5]. This algorithm has been validated using the data sets provided by the Retrospective Image Registration Evaluation Project (RIRE) at Vanderbilt University [7]. Non-rigid registration is required to register patient data to the atlas and vice versa. In one embodiment, non-rigid registration is performed on MR image volumes using an algorithm proposed recently [6]. This algorithm computes a deformation field that is modeled as a linear combination of radial basis functions with finite support. The similarity measure used in the algorithm is the mutual information between the images. In practice, two transformations (one from the atlas to the patient and the other from the patient to the atlas) are computed simultaneously, which are constrained to be inverses of each other.

The validation of non-rigid registration algorithms is an open-ended problem. However, it has been has demonstrated the ability to register accurately MR volumes for STN-DBS implantation, where twenty-one (21) patents with a total of thirty-nine (39) electrodes were evaluated, and the final intra-operative positions of the implants were respectively mapped onto the atlas [77]. FIG. 1 shows the atlas coordinates projected from the spatial coordinates of the DBS positions acquired intra-operatively from the right. STN on (a) axial and (b) sagittal views (similar results were found for the left side). Each circle 110 corresponds to an atlas position of a final DBS target projected onto the atlas. To orient the reader, contours 120 of anatomic structures obtained from the Schaltenbrand-Wahren atlas were superimposed onto the MR slice passing through the centroid of the cloud of points. This was done by registering manually the Schaltenbrand-Wahren atlas to the atlas according to the present invention using the Voxim software (IVS Solutions AG, Chemnitz, Germany). FIG. 1 shows that the final target points 110 chosen intra-operatively cluster tightly around the same sub-region of the STN, as would be expected. This, in turn, indicates that the patient's image volumes can be accurately registered to the atlas.

Electrophysiological Atlas Maps

According to the present invention, an atlas is created to contain electrophysiological information acquired from a population of patients. In the electrophysiological atlas, any spatial coordinates of the brain of a patient are related to atlas coordinates in the atlas in a way such that the electrophysiological information associated with spatial coordinates from which it is acquired in the brain of the patient can be related to atlas coordinates in the atlas, and vice versa.

The acquired electrophysiological information at least includes intra-operative information for each patient. The intra-operative information may include information associated with one or more microelectrodes, where the information includes microelectrode recordings, a position of the microelectrode recordings, a label of a structure in which the microelectrode recordings is located, and others. The microelectrode recordings can be characterized by a firing rate that measures tonic activity and indices that measures phasic activity, where the indices include a burst index, a pause ratio, a pause index, and an interspike interval histogram. Other characteristic features may also be extracted from the microelectrode recordings and can also be utilized. The intra-operative information may also includes information associated with one or more stimulation electrodes, where the information includes voltages applied to the at least one stimulation electrode, a response of a target of interest undergoing treatment to the stimulation, differences in voltage between disappearance of symptoms and appearance of side effects, a position of the at least one stimulation electrode, a final intra-operative target position of a deep brain stimulator to be placed, and any mixture thereof. The response of the target of interest undergoing treatment to the stimulation includes loss of rigidity, location where the loss of rigidity is observed, appearance of side effects, and/or location affected by these side effects. The information may be used for the surgical team to optimize the final potion of a DBS implant and DBS programming for a patient.

The intra-operative information may have information associated with one or more deep brain stimulators implanted in the brain of each patient. The information may include the positions of the one or more deep brain stimulators in post-operative CT images, optimal settings of the one or more deep brain stimulators, overall assessment of the patient after implant of the one or more deep brain stimulators, and the likes.

Because the image coordinates of the points (positions) at which the (electrophysiological information) signals are recorded are known, one can extract features from these acquired signals, and then map the value of these extracted features onto the electrophysiological atlas. In one embodiment, the electrophysiological atlas corresponds to a database. In the database, each signal is stored with its spatial coordinates in the image volume and its corresponding coordinates in the electrophysiological atlas. The database can be accessed by queries and returns for example a list of records, and each of the queries is pointed to a file that contains a signal. These signals can be processed and features extracted. The extracted features are then stored in that database and can be accessed in the same way. This permits the creation of multiple atlases in the database, each for a corresponding feature.

Figure 2:
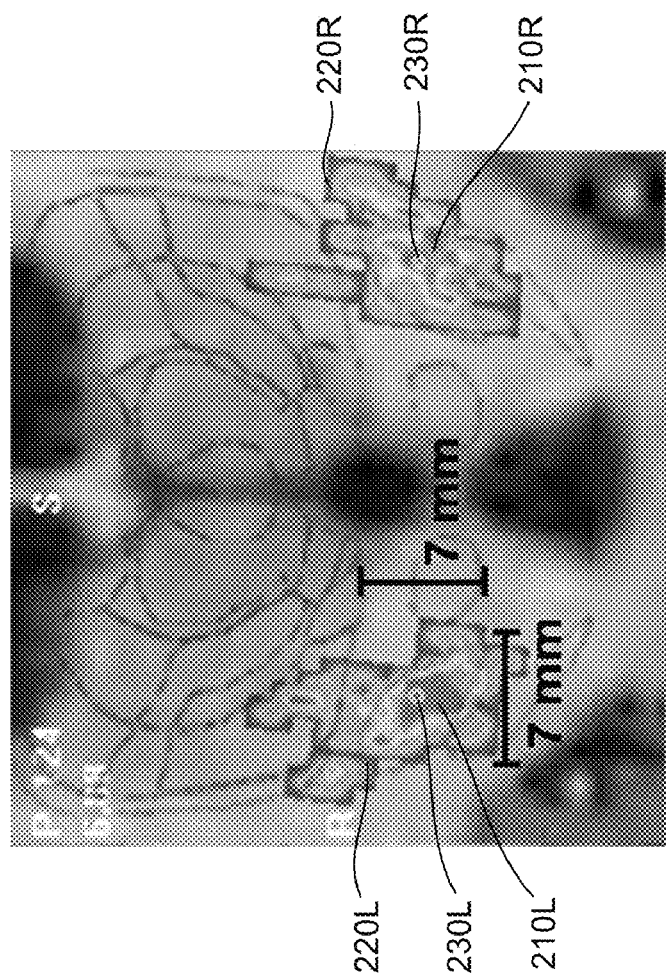
FIG. 2 shows a color-coded electrophysiological atlas map corresponding to the spike rate, i.e., the number of spikes/second, according to one embodiment of the present invention, where red color areas (210L and 210R) correspond to the regions of anatomic structures in which the spike rate has high values, blue color areas (220L and 220R) correspond to the regions of anatomic structures in which the spike rate has low values, and a small white circle (230L and 230R) corresponds to the optimal target point (position) in the atlas.

It has been known that the boundaries of nuclei and sub-nuclei are not visible in anatomic CT and MR images but that these boundaries are inferred intra-operatively from MERs and responses to stimulations. Thus, these extracted features can be used to detect structures of interest and/or boundaries of the structures. For example, according to the present invention these boundaries of nuclei and subnuclei can be resolved and visualized in the electrophysiological atlas, based on these features extracted from MER signals, as shown in FIG. 2. In these figures, regions that correspond to low and high values for some of these features are identified in the electrophysiological atlas. To generate these maps, the features have been computed for each signal of each patient, mapped onto the electrophysiological atlas, and then averaged over the number of the signals. FIG. 2 shows a color coded atlas map that corresponds to the spike rate, i.e., the number of spikes/second. In this atlas map, areas 210L and 210R (in a red color) correspond to the regions of anatomic structures where the spike rate extracted from MER signals recorded in the regions has high values, while areas 220L and 220R (in a blue color) correspond to the regions of anatomic structures where the spike rate extracted from MER signals recorded in the regions has low values. The optimal target point (position) in the atlas is shown with a small circle 230L or 230R (in a white color). This atlas map shows that a region having high values of the spike rate corresponds to the STN, as shown by the contours obtained from the Schaltenbrand-Wahren atlas. It is noted that a small misalignment of these STN contours and the region of high spike rate on the right side, which is attributed to the difficulty of registering the Schaltenbrand-Wahren atlas with the MR volume.

Since the correspondence between patient and atlas coordinates has been established in the electrophysiological atlas, one can query the database for individual extracted features and/or any combinations of the extracted features and visualized them in the electrophysiological atlas. The extracted features include, for example, the spike frequency, PSD, BI (burst index), PI (pause index), PR (pause ratio), CV (coefficient of variation), mISI (mean interspike interval) and FR (firing rate). Other features can be extracted as new features extraction algorithms are developed, making the electrophysiological atlas completely dynamic. Additionally, the electrophysiological atlas can be populated with newly acquired electrophysiological information from new patients, and therefore is updatable.

Figure 3:
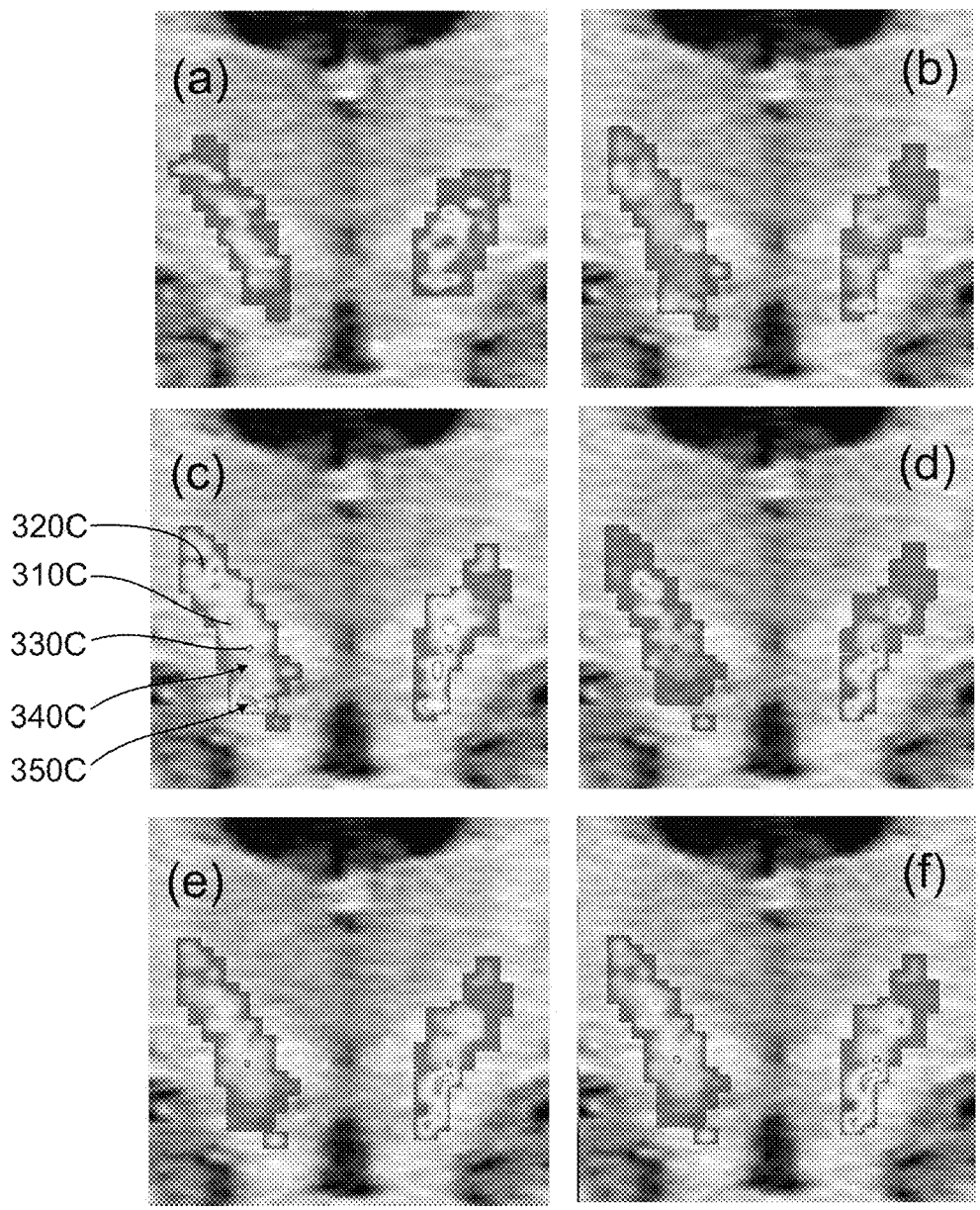
FIG. 3 shows color-coded electrophysiological atlas maps corresponding to different extracted features according to one embodiment of the present invention: (a) a burst index map; (b) a pause ratio map; (c) a pause index map; (d) a power spectral density map, (e) a mean value map of the fifth detail component of the wavelet decomposition, and (f) a standard deviation map of the fifth detail component of the wavelet decomposition, where red color areas correspond to the regions of anatomic structures in which the corresponding extracted feature has high values, blue color areas correspond to the regions of anatomic structures in which the corresponding extracted feature has low values, and a small white circle corresponds to the optimal target point (position) in the atlas.

FIG. 3 shows color-coded electrophysiological atlas maps corresponding to different extracted features including (a) a burst index map; (b) a pause ratio map; (c) a pause index map; (d) a power spectral density map, (e) a mean value map of the fifth detail component of the wavelet decomposition, and (f) a standard deviation map of the fifth detail component of the wavelet decomposition. In these features maps, red color areas, e.g., 310C, correspond to the regions of anatomic structures where the corresponding extracted feature extracted from signals recorded in the regions has high values, while blue color areas, e.g., 320C, correspond to the regions of anatomic structures in which the corresponding extracted feature extracted from signals recorded in the regions has low values. A small white circle, e.g., 330C, corresponds to the optimal target point (position) in the atlas. The map of the pause index shown in FIG. 3c presents good discrimination between STN and SNr nuclei, where a continuous green region around the STN 340C and a lower, a redder zone corresponds to the SNr region 350C. Clearly, this does not appear in FIG. 3d. These maps could add information that will help to discriminate sub-structures of sub-electrophysiological regions. FIGS. 3e and 3f show the mean and standard deviation of the fifth detail wavelet component. Both figures present similar clustering. Theses maps are useful to discriminate between STN (substantially high values) and SNR (high values) from the rest of the signals.

Figure 4:
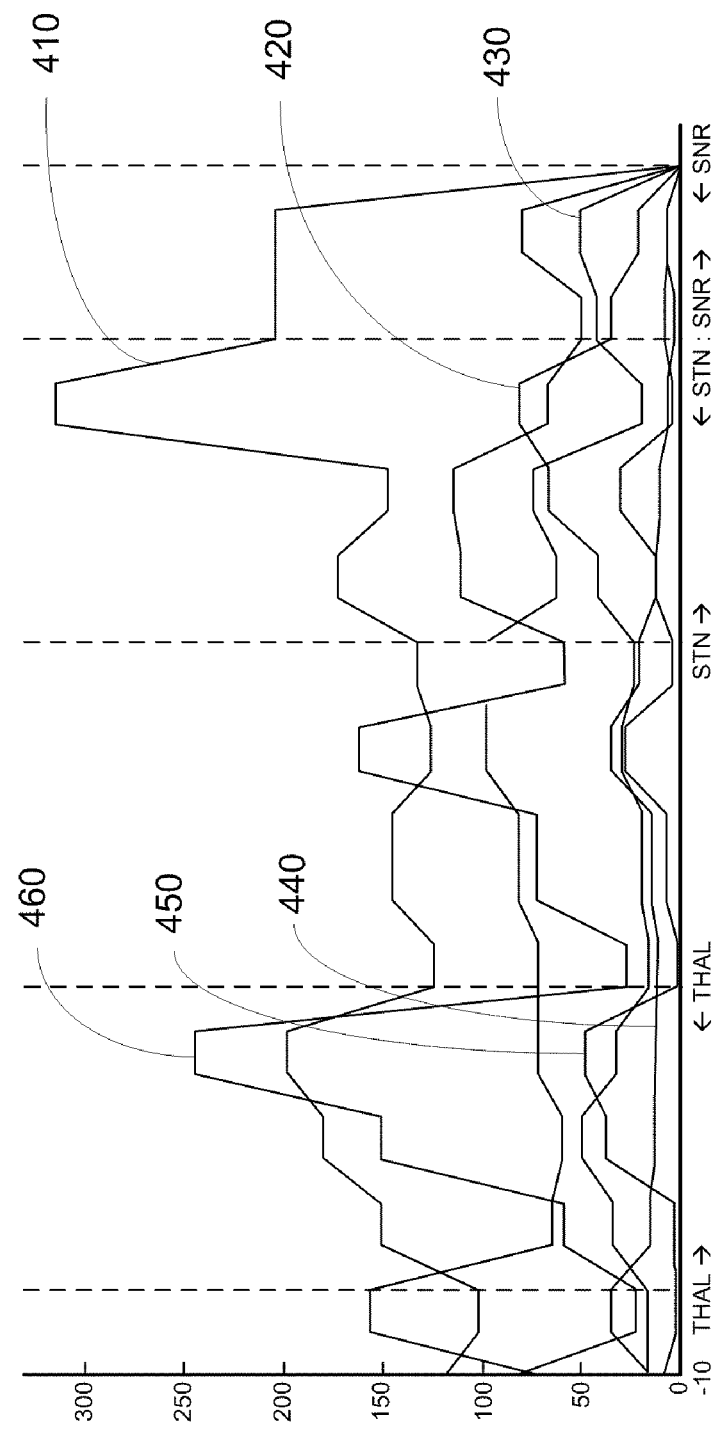
FIG. 4 shows several features histogram extracted on a usual path while targeting the STN from the features maps according to one embodiment of the present invention, where Thalamus (THAL), STN and SNr are manually labeled, and the curves are corresponding to the number of spikes (410), the burst index (420), the power spectral density (430), the pause ratio (440), the pause index (450) and the standard deviation of the fifth component of the wavelet decomposition (460), respectively.

FIG. 4 shows the same results in an alternative way. Each curve represents one feature along the same track from a regular entry point to the STN on the atlas going from −10 mm to +5 mm around the target. Thalamus, STN and SNR were manually labeled based on the signals. These curves in FIG. 4 are the number of spikes 410, the burst index 420, the power spectral density 430, the pause ratio 440, the pause index 450 and the standard deviation of the fifth component of the wavelet decomposition 460, respectively. Curve for the number of spikes 410, BI 420 or the fifth wavelet component 460 shows patterns corresponding to the manual labels. Accordingly, each feature can be used for microelectrode recording discrimination.

Intra-Operative Efficacy Atlas

Intra-operative micro- or macro-stimulation is used to determine suitable targets in which the stimulation induces the best improvement of motor symptoms, especially rigidity and tremor without adverse effects. While targeting the STN, the stimulation is applied approximately every 2 mm along the track, starting at the boundary of the STN, which is determined by micro-electrode recordings (MERs) acquired prior to the stimulation. At every position, the stimulation is typically performed with voltages starting at 0.5 V up to 5 V by 0.5 V increments. The effect of the stimulation on rigidity, muscle tone, bradykinesia, paresthesias, muscle contraction, eye movements and subjective sensations are assessed for every applied voltage. The optimal voltage is determined at each position and the percentage of the loss of rigidity is recorded for this voltage. Because the intra-operative coordinates of a patient's electrode can be mapped onto the atlas, any information acquired intra-operatively can be projected onto the atlas. This, in turn, permits the creation of a number of statistical maps relating spatial coordinates in the atlas to characteristics measured intra-operatively. As shown above, maps of features extracted from MERs can be created visually, where the maps of the mean spike rate can be used to define the boundary of the STN in the atlas.

According to the present invention, a stimulation map can be created to associate each atlas position with an efficacy of stimulation at a corresponding stimulation position at which an electrode contact is located. The stimulation map provides useful information to the neurologist for programming. In one embodiment, an efficacy of stimulation at a stimulation position is defined as being (1) inversely proportional to a voltage, V, applied to the stimulation position; (2) proportional to the percentage of loss of rigidity, $L^R$, caused by the applied voltage V, and (3) proportional to a therapeutic window that equals to the difference in voltage required to achieve the loss of rigidity (V) and the voltage for which side effects occur ($V^{SE}$), that is the efficacy of stimulation at a stimulation position is defined in the form of:

$$E = L^R * (V^{SE} - V) * \frac{1}{V}.$$

A stimulation position is regarded as an optimal stimulation position if the percentage of the loss of rigidity $L^R$ is high, the applied voltage V is low, and the difference between $V^{SE}$ and V is large. In other words, the stimulation of an electrode contact at such a position has the highest probability to be the most clinically effective.

Figure 5:
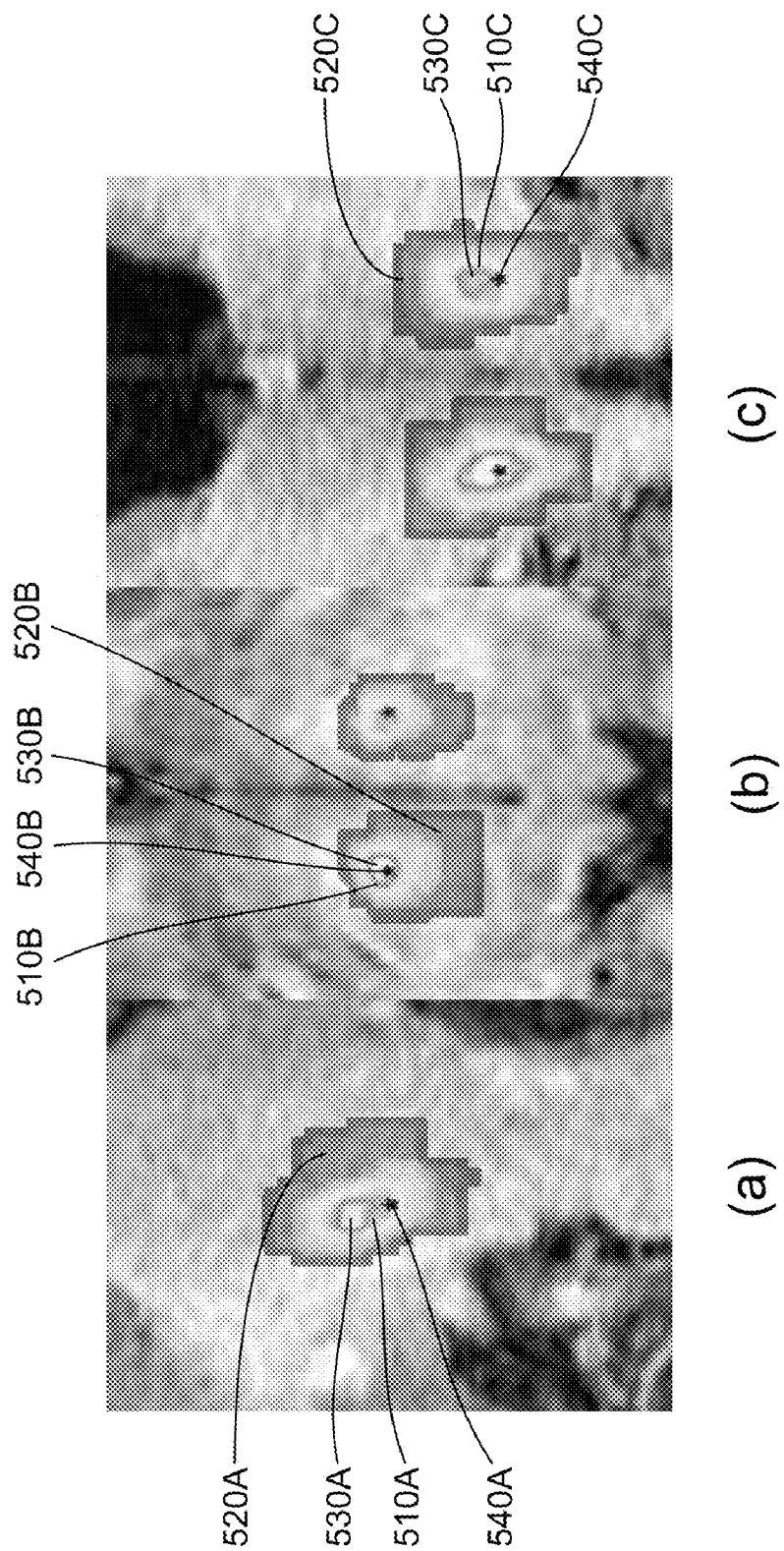
FIG. 5 shows stimulation maps according to one embodiment of the present invention, where red color areas correspond to the regions of anatomic structures in which the stimulation has a high probability to get desired stimulation results, blue color areas correspond to the regions of anatomic structures in which the stimulation has a low probability to get desired stimulation results, white color areas correspond to the regions of anatomic structures in which the stimulation has the highest probability to get desired stimulation results, and the star represents the optimal position in the atlas at which the implant is placed when targeting the STN.

By applying procedures similar to those of generating a feature map in the electrophysiological atlas as disclosed above, a stimulation map can be created in which each position in the atlas is associated with an efficacy of stimulation at a corresponding stimulation position at which an electrode contact is located. FIG. 5 shows stimulation regions mapped onto the atlas according to one embodiment of the present invention. In these maps shown in FIGS. 5a-5c, areas 510A-510C (in a red color) correspond to the regions of anatomic structures in which the stimulation has a high efficacy (probability) to get desired stimulation results, areas 520A-520C (in a blue color) correspond to the regions of anatomic structures in which the stimulation has a low efficacy (probability) to get desired stimulation results, while areas 530A-530C (in a white color) correspond to the regions of anatomic structures in which the stimulation has the highest efficacy (probability) to get desired stimulation results. The star 540A-540C represents the optimal position in the atlas at which the implant is placed when targeting the STN.

Alternatively, the stimulation map can be created with each stimulation point in the atlas being modeled by a Gaussian curve; where the height of the curve is a function of the efficacy and the radius a function of the stimulation voltage. Specifically, the creation of an efficacy map is as follows: at first, stimulation data corresponding to a target region in which a deep brain stimulator is implanted are obtained from a database (electrophysiological atlas). The stimulation data comprise M×N sets of intra-operatively acquired stimulation signals, $\{V_{ij}, L_{ij}^R, V_{ij}^{SE}\}$, and their corresponding stimulation positions, $\{x_j, y_j, z_j\}$, mapped onto the electrophysiological atlas, where i=1, 2, ..., M, M being a positive integer and the number of a population of patients from which the stimulation signals are acquired and stored in the database, In one embodiment, M=30. j=1, 2, ..., N, N being a positive integer and the number of positions at which the stimulation takes place for each of the population of patients. $V_{ij}, L_{ij}^R, V_{ij}^{SE}$ are a stimulation voltage, a percent of loss of rigidity caused by the stimulation voltage, and a voltage for which side effects occur, respectively, at the j-th stimulation position of the i-th patient.

Secondly, a local efficacy of stimulation, $E_{ij}$, at the j-th stimulation position ($x_j, y_j, z_j$) for the i-th patient is modeled with a Gaussian curve, $F_{ij}$. The Gaussian curve $F_{ij}$ is defined to be the form of:

$$F_{ij} = E_{ij} * \exp\left[-\left(\frac{x_j^2 + y_j^2 + z_j^2}{2V_{ij}^2}\right)\right],$$

where the local efficacy of stimulation $$E_{ij} = L_{ij}^R * (V_{ij}^{SE} - V_{ij}) * \frac{1}{V_{ij}},$$

and the height of the Gaussian curve $F_{ij}$ is a function of the local efficacy of stimulation $E_{ij}$, and the radius of the Gaussian curve $F_{ij}$ is a function of the stimulation voltage $V_{ij}$.

Then, repeatedly modeling the efficacy of stimulation at the j-th stimulation position ($x_j, y_j, z_j$) for each of the population of patients, i=1, 2, ..., M, results in M sets of Gaussian curves $\{F_{ij}\}$ for the j-th stimulation position ($x_j, y_j, z_j$). The M sets of Gaussian curves $\{F_{ij}\}$ are averaged to obtain an efficacy of stimulation at the j-th stimulation position ($x_j, y_j, z_j$), which is equal to the mean value of the M sets of Gaussian curves $\{F_{ij}\}$.

Repeating the above processes for each of the stimulation positions, j=1, 2, ..., N, to obtain N efficacies of stimulation respectively at the N stimulation positions, thereby creating an efficacy atlas in which any spatial coordinates of the brain of the patient are related to atlas coordinates of the efficacy atlas, and each position in the atlas coordinates of the efficacy atlas is associated with an efficacy of stimulation at a corresponding position in the spatial coordinates of the brain of the patient.

Accordingly, a point (position) with a small stimulation voltage and a high percentage of the loss of rigidity is thus associated with a curve with a small standard deviation and large amplitude. In other words, a point (position) associated with a curve that has a small standard deviation and large amplitude has a large but localized effect on the atlas, while a point (position) with a large standard deviation has a smaller impact that extends over a larger region.

Figure 6:
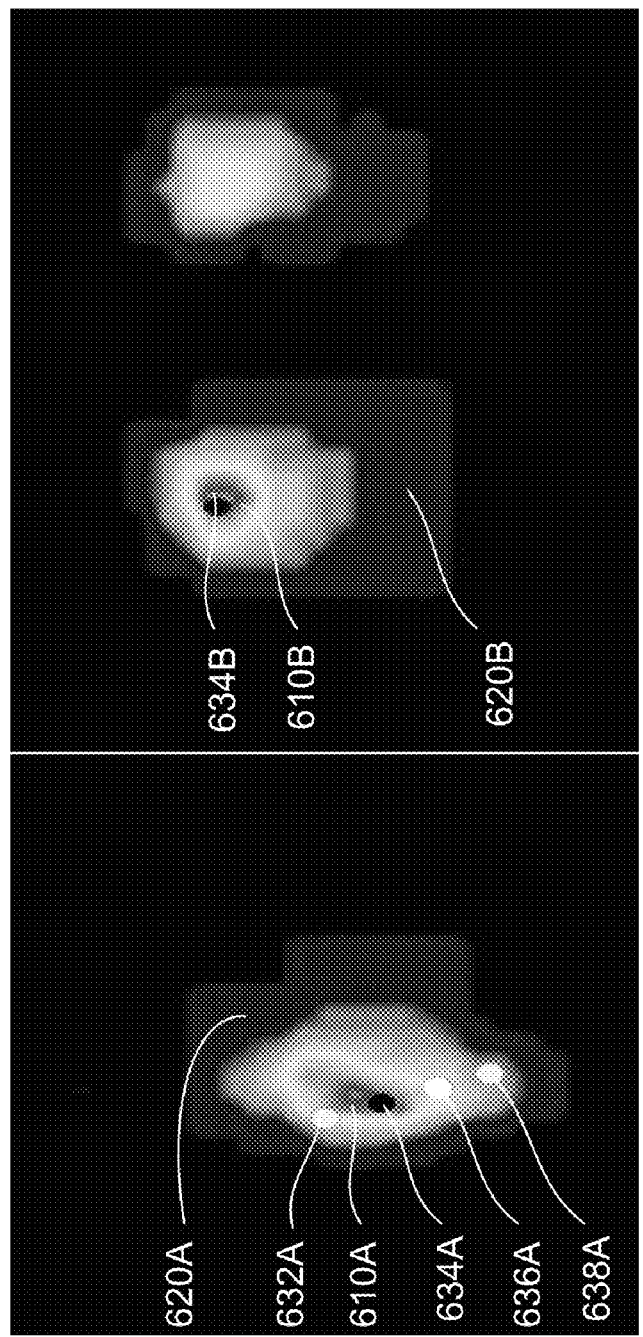
FIG. 6 shows the position of a four-contact electrode lead implanted into a brain of a patient mapped onto a stimulation map according to one embodiment of the present invention, where the contact that has been used for programming is in a black color.

Referring to FIG. 6, stimulation maps is shown according to one embodiment of the present invention. In these maps shown in FIGS. 6*a* and 6*b*, areas 610A and 610B (in a red color) correspond to the regions of anatomic structures in which the stimulation has a high efficacy (probability) to get desired stimulation results, while areas 620A and 620B (in a blue color) correspond to the regions of anatomic structures in which the stimulation has a low efficacy (probability) to get desired stimulation results. As shown in FIG. 6*a*, each position of four contacts 632A, 634A, 636A and 638A of the electrode lead implanted into a brain of a patient is mapped onto the stimulation map. In this exemplar example, contacts 634A and 634B are used for programming is in black. To alleviate the symptoms, the contact tension is about 1 V.

Figure 7:
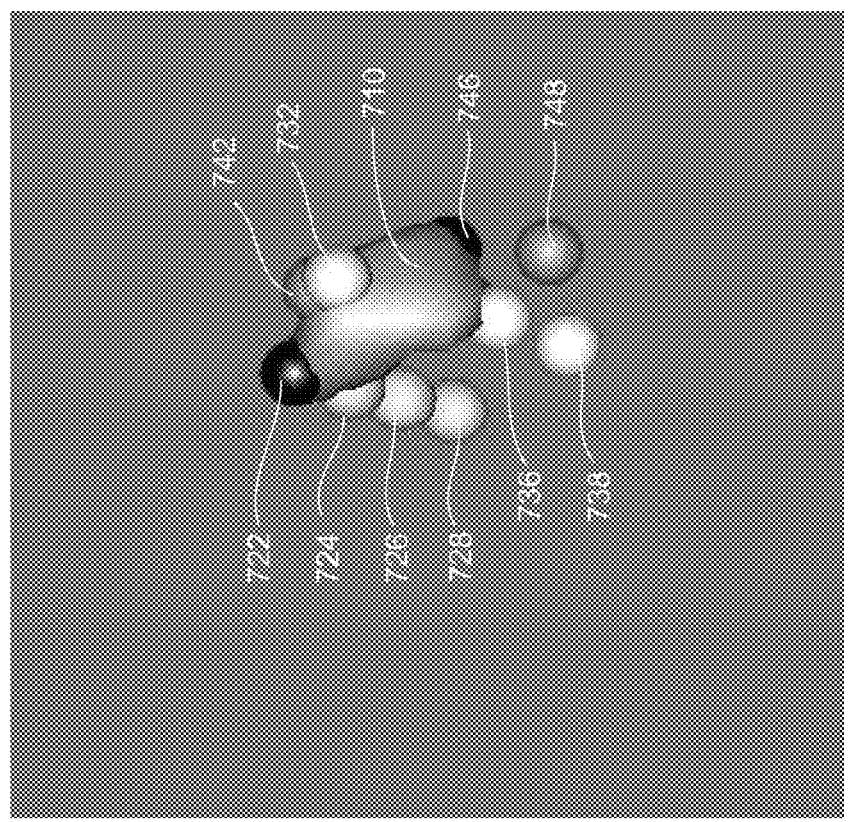
FIG. 7 shows a three-dimensional (3D) view of the positions of three four-contact electrode leads respectively implanted into brains of three patients mapped onto the stimulation atlas, where the contacts used for programming are in a black color.

FIG. 7 shows a perspective view of a 3D stimulation map for three patients with each patient having a four-contact electrode implanted in the target region. In FIG. 7, stimulation region 710 (in a red color) represents the iso-surface in the efficacy map that corresponds to an iso-intensity value of 85%. Spheres 722, 724, 726 and 728 respectively represent the four contacts of the electrode implanted in the target region of a first patient. Spheres 732, 736 and 738 respectively represent the three contacts (one is not shown) of the electrode implanted in the target region of a second patient. Spheres 742, 746 and 748 respectively represent the three contacts (one is not shown) of the electrode implanted in the target region of a third patient. For the electrode implanted in the target region of the first patient, spheres 722 is the contact that has been selected by the neurologist as the optimum contact, while the electrode implanted in the target region of the third patient, spheres 746 is the contact that has been selected by the neurologist as the optimum contact. The map shows that for these cases, the neurologist has chosen the electrode contact that has the highest probability of being effective as predicted by the efficacy map according to the present invention. To alleviate the symptoms the contact tension for the three cases is around 1 V.

Atlas-Based Contact Selection

Once the efficacy atlas is created, it can be used post-operatively to assist the neurologist in selecting the optimum contact for stimulation. To achieve this, a position of each electrode contact of a stimulation lead implanted into a target region of a brain of a patient needs to be known, and then is mapped onto the efficacy atlas so as to determine its efficacy of stimulation at the position. This can be done by querying the database for the final position of each electrode contact of the stimulation lead implanted in the target region of the brain of the patient, or by acquiring post-operatively the position of each electrode contact of the stimulation lead implanted in the target region of the brain of the patient. The contact that falls into the stimulation regions on the atlas corresponding to the highest probability of good efficacy would be the optimum contact for stimulation.

Results and Discussion

Figure 8:
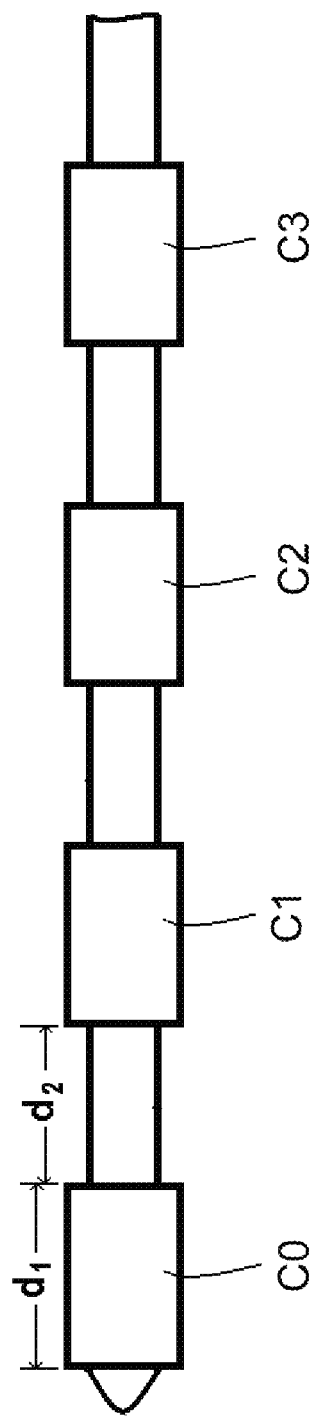
FIG. 8 schematically shows one example of a quadricpolar deep brain stimulator that can be utilized to practice the present invention.

Table 1 lists quantitative results obtained with the method according to the present invention. The efficacy probability from the atlas was correlated to each contact in the 17 subjects included in this exemplary embodiment. The DBS leads implanted in these patients are a Medtronic 3389 quadripolar Lead®, which has four contacts C0, C1, C2 and C3. Each of the four contacts C0, C1, C2 and C3 has a length, $d_1$, which is about 0.5 mm, and the distance, $d_2$, between two neighboring contacts, for example, C0 and C1, is about 0.5 mm, as shown in FIG. 8.

In Table 1, the numbers in bold and italic are the contacts selected by the neurologist. Contacts are numbered from C0 (distal contact) to C3 (proximal contact). The column labeled "V" is the amplitude of the therapeutic voltage.

TABLE 1

The table shows, for 17 STN patients, the likelihood of the four contacts to get good stimulation results. The number in bold and italic shows the contact that was selected as the best one by the neurologist. Contacts are numbered from C0 (bottom contact) to C3 (top contact). The implant used for these patients is a Medtronic 3389 implant. The size of the contact is 0.5 mm and the gap between the contacts is 0.5 mm.

| Patient | Left | | | | | Right | | | | |
|---|---|---|---|---|---|---|---|---|---|---|
| | C0 | C1 | C2 | C3 | V | C0 | C1 | C2 | C3 | V |
| P0 | 0.47 | *0.77* | *0.84* | 0.61 | 1.1 | *NI* | 0.1 | 0.2 | 0.3 | 1.1 |
| P1 | 0.18 | 0.53 | *0.55* | 0.71 | 2.2 | 0.2 | *0.4* | 0.6 | 0.7 | 2.2 |
| P2 | 0.53 | 0.84 | *0.94* | 0.61 | 2.4 | 0.4 | 0.7 | *0.9* | 1.0 | 1.7 |
| P3 | 0.64 | 0.78 | *0.69* | 0.27 | 1.5 | 0.2 | 0.4 | *0.7* | 1.0 | 1.3 |
| P4 | 0.06 | 0.07 | *0.10* | 0.24 | 1.5 | 0.3 | 0.6 | *0.7* | 0.4 | 1.8 |
| P5 | 0.01 | 0.11 | 0.12 | *0.30* | 1.8 | | | | | |
| P6 | 0.74 | 0.74 | *0.69* | 0.47 | 1.5 | 0.4 | 0.7 | *0.8* | 0.7 | 1.5 |
| P7 | 0.65 | 0.59 | *0.47* | 0.21 | 1.6 | 0.7 | 0.9 | 1.0 | *0.9* | 1.7 |
| P8 | 0.80 | 0.47 | *0.23* | 0.10 | 1.4 | | | | | |
| P9 | 0.73 | 0.98 | *0.93* | 0.65 | 2.3 | 0.8 | *0.9* | 0.8 | 0.4 | 2.2 |
| P10 | 0.72 | 0.84 | *0.84* | 0.59 | 3.2 | 0.3 | *0.6* | 0.6 | 0.4 | 3.2 |
| P11 | 0.59 | 0.85 | *0.90* | 0.65 | 1.8 | 0.2 | 0.4 | *0.6* | 0.9 | 1.5 |
| P12 | 0.60 | 0.49 | *0.41* | 0.11 | 2.1 | 0.2 | 0.4 | *0.6* | *0.5* | 2.7 |
| P13 | | | | | | 0.9 | *1.0* | 0.9 | *0.8* | 2.3 |
| P14 | *0.12* | 0.47 | 0.84 | 0.84 | 0.8 | NI | 0.1 | *0.2* | 0.4 | 1.0 |
| P15 | 0.73 | *0.91* | 0.80 | 0.40 | 1.5 | 0.3 | *0.5* | 0.7 | 0.6 | 1.5 |
| P16 | 0.85 | 0.92 | 0.69 | *0.50* | 1.8 | 0.3 | 0.6 | *0.7* | 0.6 | 1.8 |
| P17 | | | | | | 0.2 | *0.4* | 0.7 | 1.0 | 3.2 |

Results presented in Table 1 show that about 60% of the contacts selected by the neurologist are the contacts with the highest efficacy probability in the efficacy atlas. This indicates the feasibility of using a statistical atlas to facilitate the programming process. A more detailed analysis of this process also suggests that using predictions from the efficacy atlas shortens the time required to reach stable programming. For example, programming notes from the neurologists for patient P3 showed that contact C1 was tried first on the right side before moving to C2 which produced better results. For patient P11 the C0 contacts were first tried on both sides before moving to contacts C2. A similar trend had been observed for the left implant in patient P12, where the neurologist tried the stimulation of the contacts from contact C3 to C2. For patient P15, contact C1 on the left side was observed to have a better effect on rigidity than contact C2.

For a few cases, the optimal electrode predicted by the atlas has been tried and rejected. For example, in patient P16, contacts C0 and C1 were tried but not selected because these caused significant side effects. These effects were reduced with contact C3 but this particular patient still has significant rigidity and bradykinesia.

In the present invention, among other things, a method for programming a deep brain stimulator for optimal stimulation and a computerized system utilized the method are disclosed, which facilitate one of the bottlenecks of DBS therapy: the IPG (Internal Pulse Generator) programming. This is achieved by creating an efficacy atlas from an electrophysiological atlas, where each position in the atlas coordinates in the efficacy atlas is associated with an efficacy of stimulation at a corresponding position in spatial coordinates of a brain of a patient, and then correlating the position of each electrode contact of a stimulation electrode implanted in the brain of the patient with a corresponding efficacy contained in the efficacy atlas so as to determine which of the contacts has the highest probability (efficacy) to be the most clinically effective.

Additional improvements may be made. First, a prospective validation study is initiated. Rather than verifying that the electrode is the optimal one after programming has been completed, the optimal contact is proposed to the neurologist at the time of initial programming. This approach has been applied when developing and validating the automatic preoperative target prediction for DBS implantation [7]. Second, at the time of programming, the neurologist is provided with a 3D display of the position of the electrodes in the efficacy map overlaid on high resolution MR images. This permits correlation of these positions with anatomy, thereby facilitating spatial orientation and navigation between the contacts. Third, as the number of patients increases, maps of side effects would be created. Currently, only is a crude definition of efficacy used: reduction in rigidity weighted by the therapeutic voltage window (i.e., the difference between the voltage required to suppress the symptoms and voltage inducing side effects). This definition would be refined to improve the way side effects are taken into consideration. To achieve this, maps of side effects would be created. This permits an automatic multi-parameter optimization procedure that will minimize side effects while maximizing the positive effects of the stimulation. Finally, the electric field produced by a specific stimulation configuration is modeled and this electric field is superimposed on the efficacy and side effect maps. This permits the neurologist to visualize interactively the effect of parameter settings on the region being affected and facilitate multi-electrode programming.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] Pollak P, Krack P, Fraix V, et al. Intraoperative micro- and macrostimulation of the STN in Parkinson's disease. Mov Disorders, 2002; 17(Suppl. 3):S155-S161.

[2] Volkmann J, Herzog J, Kopper F, Deuschl G. Introduction to the programming of deep brain stimulation. Mov Disord 2002; 17(Suppl. 3):S181-S187.

[3] R. G. Deuschl, J. Volkmann, and P. Krack, "Deep brain stimulation for movement disorders," Movement Disorders, vol. 17, no. 3, pp. S1-S11, March/April. 2002.

[4] B. Schrader, W. Hamel, D. Weinert, and H. M. Mehdom, "Documentation of electrode localization." Movement Disorders, vol. 17, no. 3, pp. S167-S174, 2002.

[5] L. Rui, "Automatic placement of regions of interest in medical images using image registration," Master thesis in Electrical Engineering 2001.

[6] G. K. Rohde, A. Aldroubi, and B. M. Dawant, "The adaptive bases algorithm for intensity based nonrigid image registration," registration," IEEE Transactions on Medical Imaging, vol. 22, pp. 1470-1479, 2003.

[7] P. F. D'Haese, E. Cetinkaya, P. E. Konrad, C. Kao, B. M. Dawant, "Computer-aided placement of deep brain stimulators: from planning to intraoperative guidance" IEEE Transactions on Medical Imaging, vol. 24 (11), pp. 1469-78, November 2005.

[8] Fitzpatrick J M, Konrad P E, Nickele Ch, Cetinkaya E, and Kao Ch: Accuracy of Customized Miniature Stereotactic Platforms.

What is claimed is:

1. A method for programming a deep brain stimulator implanted in a target region of a brain of a living subject for optimal stimulation, wherein the deep brain stimulator comprises at least one electrode having a plurality of electrode contacts spaced apart from each other, and wherein any portion of the brain of the living subject is identifiable by a set of corresponding spatial coordinates, comprising the steps of:

(a) creating an efficacy atlas in which any spatial coordinates for a position in a target region of the brain of the living subject are related to a position with corresponding atlas coordinates in the efficacy atlas, and each position in the atlas coordinates of the efficacy atlas is associated with an efficacy of stimulation at a corresponding position in the spatial coordinates of the brain of the living subject;

(b) acquiring a position of each electrode contact of the at least one electrode in the spatial coordinates of the brain of the living subject;

(c) mapping the acquired position of each electrode contact of the at least one electrode in the spatial coordinates of the brain of the living subject onto a corresponding position in the efficacy atlas so as to determine the efficacy of stimulation at the acquired position in the spatial coordinates of the brain of the living subject; and (d) selecting one or more electrode contacts having the highest efficacy for stimulation, wherein the efficacy of stimulation at a position in the spatial coordinates of the brain of the living subject is proportional to a percent of loss of rigidity, $L^R$, proportional to a therapeutic window that equals to the difference between a voltage, V, applied to the position for achieving the loss of rigidity and a voltage, $V^{SE}$, applied to the position for which side effects occur, and inversely proportional to the voltage V, wherein the efficacy of stimulation at a position is corresponding to the probability of the stimulation to be clinically effective at the position, and wherein the creating step (a) comprises the steps of:

(i) obtaining stimulation data corresponding to a target region in which a deep brain stimulator is implanted from a database, wherein the stimulation data comprise M×N sets of intra-operatively acquired stimulation signals, $\{V_{ij}, L_{ij}^R, V_{ij}^{SE}\}$, and their corresponding stimulation positions, $\{x_j, y_j, z_j\}$, wherein i=1, 2, ..., M, M being a positive integer and the number of a population of living subjects from which the stimulation signals are acquired and stored in the database, and j=1, 2, ..., N, N being a positive integer and the number of positions at which the stimulation takes place for each of the population of living subjects, and wherein $V_{ij}, L_{ij}^R, V_{ij}^{SE}$ are a stimulation voltage, a percent of loss of rigidity caused by the stimulation voltage, and a voltage for which side effects occur, respectively, at the j-th stimulation position of the i-th living subject;

(ii) choosing a local efficacy of stimulation, $E_{ij}$, at the j-th stimulation position $(x_j, y_j, z_j)$ for the i-th living subject with a Gaussian curve, $F_{ij}$, in the form of:

$$F_{ij} = E_{ij} * \exp\left[-\left(\frac{x_j^2 + y_j^2 + z_j^2}{2V_{ij}^2}\right)\right],$$

wherein the local efficacy of stimulation $$E_{ij} = L_{ij}^R * (V_{ij}^{SE} - V_{ij}) * \frac{1}{V_{ij}};$$

and wherein the height of the Gaussian curve $F_{ij}$ is a function of the local efficacy of stimulation $E_{ij}$, and the radius of the Gaussian curve $F_{ij}$ is a function of the stimulation voltage $V_{ij}$;

(iii) repeating step (ii) for each of the population of living subjects, i=1, 2, ..., M, so as to obtain M sets of Gaussian curves $\{F_{ij}\}$ for the j-th stimulation position $(x_j, y_j, z_j)$;

(iv) averaging the M sets of Gaussian curves $\{F_{ij}\}$ to obtain an efficacy of stimulation at the j-th stimulation position $(x_j, y_j, z_j)$, which is equal to the mean value of the M sets of Gaussian curves $\{F_{ij}\}$; and (v) repeating steps (ii)-(iv) for each of the stimulation positions, j=1, 2, ..., N, to obtain N efficacies of stimulation respectively for the N stimulation positions, thereby creating the efficacy atlas.

2. The method of claim 1, wherein the efficacy atlas comprises at least one stimulation map having at least one stimulation region corresponding to the target region of the brain of the living subject for optimal stimulation.

3. The method of claim 1, wherein the database comprises an electrophysiological atlas containing electrophysiological information acquired from each of the population of living subjects and related to atlas coordinates of the electrophysiological atlas.

4. The method of claim 3, wherein the atlas coordinates of the efficacy atlas are substantially coincident with the atlas coordinates of the electrophysiological atlas.

5. The method of claim 3, wherein the electrophysiological information comprises at least intra-operative information for each of the population of living subjects.

6. The method of claim 5, wherein the intra-operative information comprises at least specific information associated with at least one stimulation electrode, wherein the specific information includes voltages applied to the at least one stimulation electrode, a response of a living subject undergoing treatment to the stimulation, differences in voltage between disappearance of symptoms and appearance of side effects, and a position of the at least one stimulation electrode.

7. The method of claim 6, wherein the response of the living subject undergoing treatment to the stimulation includes loss of rigidity, location where the loss of rigidity is observed, appearance of side effects, and/or location affected by the side effects.

8. The method of claim 5, wherein the intra-operative information comprises at least specific information associated with a deep brain stimulator having at least one electrode, wherein the specific information includes a position of each electrode contact of the at least one electrode, and a voltage, frequency and pulse width of stimulation at the position.

9. The method of claim 8, wherein the acquiring step comprises the step of obtaining the position of each electrode contact of the at least one electrode from the database.

10. The method of claim 1, wherein the acquiring step comprises the step of acquiring the position of each electrode contact of the at least one electrode post-operatively from the target region of the brain of the living subject in which the deep brain stimulator is implanted.

11. The method of claim 1, wherein the mapping step is performed with a non-rigid registration algorithm.

12. A method for programming a deep brain stimulator implanted in a target region of a brain of a living subject for optimal stimulation, wherein the deep brain stimulator comprises at least one electrode having a plurality of electrode contacts, comprising the step of:

(a) creating an efficacy atlas in which a position in atlas coordinates of the efficacy atlas is related to a corresponding position in spatial coordinates of the brain of the living subject, and each position in atlas coordinates of the efficacy atlas is associated with an efficacy of stimulation at a corresponding position in spatial coordinates of the brain of the living subject, comprising the steps of:

(i) obtaining stimulation data corresponding to a target region in which a deep brain stimulator is implanted from a database, wherein the stimulation data comprise M×N sets of intra-operatively acquired stimulation signals, $\{V_{ij}, L_{ij}^R, V_{ij}^{SE}\}$, and their corresponding stimulation positions, $\{x_j, y_j, z_j\}$, wherein i=1, 2, ..., M, M being a positive integer and the number of a population of living subjects from which the stimulation signals are acquired and stored in the database, and j=1, 2, ..., N, N being a positive integer and the number of positions at which the stimulation takes place for each of the population of living subjects, and wherein $V_{ij}$, $L_{ij}^{R}$, $V_{ij}^{SE}$ are a stimulation voltage, a percent of loss of rigidity caused by the stimulation voltage, and a voltage for which side effects occur, respectively, at the j-th stimulation position of the i-th living subject;

(ii) choosing a local efficacy of stimulation, $E_{ij}$, at the j-th stimulation position $(x_j, y_j, z_j)$ for the i-th living subject with a Gaussian curve, $F_{ij}$, in the form of:

$$F_{ij} = E_{ij} * \exp\left[-\left(\frac{x_j^2 + y_j^2 + z_j^2}{2V_{ij}^2}\right)\right],$$

wherein the local efficacy of stimulation $$E_{ij} = L_{ij}^{R} * (V_{ij}^{SE} - V_{ij}) * \frac{1}{V_{ij}};$$

and wherein the height of the Gaussian curve $F_{ij}$ is a function of the local efficacy of stimulation $E_{ij}$, and the radius of the Gaussian curve $F_{ij}$ is a function of the stimulation voltage $V_{ij}$;

(iii) repeating step (ii) for each of the population of living subjects, i=1, 2, ..., M, so as to obtain M sets of Gaussian curves $\{f_{ij}\}$ for the j-th stimulation position $(x_j, y_j, z_j)$;

(iv) averaging the M sets of Gaussian curves $\{F_{ij}\}$ to obtain an efficacy of stimulation at the j-th stimulation position $(x_j, y_j, z_j)$, which is equal to the mean value of the M sets of Gaussian curves $\{F_{ij}\}$; and (v) repeating steps (ii)-(iv) for each of the stimulation positions, j=1, 2, ..., N, to obtain N efficacies of stimulation respectively for the N stimulation positions, thereby creating the efficacy atlas.

13. The method of claim 12, wherein the efficacy atlas comprises at least one stimulation map having at least one stimulation region related to the target region of the brain of the living subject for optimal stimulation.

14. The method of claim 12, wherein the database comprises an electrophysiological atlas containing electrophysiological information acquired from each of the population of living subjects and related to atlas coordinates of the electrophysiological atlas.

15. The method of claim 12, wherein the atlas coordinates of the efficacy atlas are is substantially coincident with the atlas coordinates of the electrophysiological atlas.

16. The method of claim 12, further comprising the steps of:
(b) mapping a position of each electrode contact of the at least one electrode in the spatial coordinates of the brain of the living subject onto a corresponding position in the atlas coordinates of the efficacy atlas so as to determine the efficacy of stimulation at the acquired position in the spatial coordinates of the brain of the living subject; and
(c) selecting one or more electrode contacts having the highest efficacy for stimulation.

17. The method of claim 16, wherein the mapping step is performed with a non-rigid registration algorithm.

* * * * *